US00PP20742P2

(12) United States Plant Patent
Carruth

(10) Patent No.: US PP20,742 P2
(45) Date of Patent: Feb. 9, 2010

(54) CLIMBING ROSE PLANT NAMED 'WEKAUSBOY'

(50) Latin Name: *Rosa hybrida*
Varietal Denomination: WEKausboy

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/291,981

(22) Filed: Nov. 13, 2008

(51) Int. Cl.
*A01H 5/00* (2006.01)

(52) U.S. Cl. ..... Plt./109

(58) Field of Classification Search ..... Plt./109
See application file for complete search history.

*Primary Examiner*—Annette H Para
(74) *Attorney, Agent, or Firm*—Christie, Parker & Hale, LLP

(57) ABSTRACT

A new variety of Climbing rose suitable for garden decoration, having flowers of multicolor yellow, pink and red coloration.

1 Drawing Sheet

Classification: The present invention relates to a new *Rosa hybrida* plant.

Variety denomination: The new plant has the varietal denomination 'WEKausboy'.

BACKGROUND OF THE INVENTION

This invention relates to a new and distinct variety of Climbing Rose. It has as its seed parent the variety known as Autumn Sunset (not patented) and as its pollen parent the variety known as Playboy (not patented).

SUMMARY OF THE INVENTION

Among the features which distinguish the new variety from other presently available and commercial rose cultivars known to the inventor are the following combinations of characteristics: its multicolor yellow, pink and red flower coloration, its numerous stipitate glands on the peduncle and surface of the bud that bear a strong moss-rose fragrance of sweet juniper, its numerous prickles of many sizes on the major stems, branches and new shoots and its very glossy bright green foliage. The plant has a spreading climbing growth habit, suitable for outdoor garden decoration.

Asexual reproduction of the new variety by budding as performed in Kern County and Pomona, Calif. shows that the foregoing and other distinguishing characteristics come true to form and are established and transmitted through succeeding asexual propagations. 'WEKausboy' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, Autumn Sunset by the following combination of characteristics: whereas 'WEKausboy' bears semi-double flowers (about 12 to 15 petals) of multicolor yellow, pink and red coloration, Autumn Sunset bears double flowers of warm apricot gold coloration with significantly heavier petalage (about 20 to 25 petals).

The new variety may be distinguished from its pollen parent, Playboy by the following combination of characteristics: whereas 'WEKausboy' bears flowers of multicolor yellow, pink and red coloration, Playboy bears flowers of orange and scarlet with a yellow eye. The new variety is classified as a climbing rose with a spreading climbing growth habit with canes about 300 cm. to about 350 cm. in length, whereas the pollen parent is classified as a floribunda rose with a significantly shorter bushy and rounded growing habit (about 75 to about 120 cm. in height).

COMPARISON WITH THE CLOSEST COMMERCIALLY AVAILABLE CULTIVAR

The new variety may be distinguished from its closest commercially available cultivar, Joseph's Coat (U.S. Plant Pat. #2,488) by the following combination of characteristics: whereas 'WEKausboy' bears semi-double flowers (about 12 to 15 petals) of multicolor yellow, pink and red coloration, Joseph's Coat bears double flowers of yellow and red coloration with significantly heavier petalage (about 23 to 28 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers in clusters of three to seven or more per stem. Flowers are borne in somewhat irregular to rounded clusters on strong medium length stems (about 26 to about 75 cm.). Outdoors, the plant blooms abundantly and nearly continuously during the growing season. The flowers have a slight tea to apple-like fragrance.

BUD

The peduncle is about 4.5 to about 6.0 cm. in length, of slender caliper (about 0.2 to about 0.3 cm. in diameter), and usually erect to sometimes somewhat bending. It is usually very rough, with numerous stipitate glands and some very small prickles. The stipitate glands bear a strong moss-rose fragrance of sweet juniper. Peduncle color is between 138A and 144A sometimes lightly suffused, especially on the side exposed to the sun, with near 183C.

Before the calyx breaks, the bud is about 1.4 to about 1.6 cm. in diameter at the widest point, about 1.8 to about 2.3 cm. in length, and pointed to ovoid in shape. The surface of the bud usually bears numerous stipitate glands and some hairs, usually with slender entire foliaceous parts extending beyond the tip of the bud about ½ or more of its length. The stipitate glands bear a strong moss-rose fragrance of sweet juniper. Bud color is between 138A and 144A sometimes moderately suffused, especially on the side exposed to the sun, with between 183C and 183B.

The sepals are about 2.8 to about 3.4 cm. in length and about 0.7 to about 1.0 cm. in width at the widest point. The outer surface color of the sepal is between 138A and 144A sometimes moderately suffused, especially on the side exposed to the sun, with between 183C and 183B. The inner surface color of the sepal is between 144D and 191C broadly bordered by between 138B and 191B. The inner surface of the sepal is covered with fine wooly tomentum; sepal margins are lined with many stipitate glands and few hairs.

The receptacle of the flower is of medium length (about 0.4 to about 0.7 cm.) and average to somewhat heavy in caliper (about 0.6 to about 0.7 cm. in diameter). The receptacle is somewhat pointed in form. Its surface is usually smooth with somewhat thick fleshy walls. The receptacle color is between 138A and 144A.

As the petals open (after the calyx breaks), the bud is about 1.6 to about 1.9 cm. in diameter at the widest point, about 2.4 to about 3.0 cm. in length, and very pointed to ovoid in form. The color of the under surfaces of the newly opened petals is between 9B and 11A, often heavily blushed, especially on the areas exposed to the sun, with as dark as between 45A and 46A. There is no visible change in coloration at the point where the petal attaches. The color of the upper surfaces of the newly opened petals is between 9A and 12A, often lightly washed with near 26C toward the petal edge. There is no visible change in coloration at the point where the petal attaches.

BLOOM

When fully open, the bloom ranges from about 8 to about 10 cm. in diameter. Petalage is semi-double with about 12 to 15 petals and about 1 to 2 petaloids irregularly arranged. When partially open, the bloom form is somewhat cupped to high centered, and the petals are moderately loosely spiraled to cupped with petal edges slightly rolled outward. When fully open, the bloom form is more flat to cupped, and the petals are more loosely cupped to slightly undulated with petal edges moderately rolled outward.

PETALS

The substance of the petals is 714 somewhat heavy and of medium thickness, with upper surfaces somewhat shiny to satiny and under surfaces more matte to slightly shiny. The petals are about 3.7 to about 4.5 cm. in length and about 4.0 to about 4.9 cm. in width at the widest point. Petal margins are entire.

The outer petals are very broadly round to somewhat obovate in shape with apices moderately rounded.

The inner petals are somewhat nearly round to broadly obovate in shape with apices moderately rounded.

Petaloids are about 2.2 to about 3.7 cm. in length and about 0.7 to about 1.1 cm. in width at the widest point. Petaloids are irregular to lanceolate in shape with irregular to rounded apices.

NEWLY OPENED FLOWER

The under surface color of the outer, intermediate and inner petals is between 9C and 11B. Any areas exposed to the sun blush with as dark as between 45A and 46A. There is no visible change in coloration at the point where the petal attaches.

The upper surface color of the outer petals is between 9C and 11B. Approximately the outer third to half of the petals, approaching the petal edge, is moderately washed with between 37C and 38D, sometimes irregularly flecked and striped with as dark as between 37A and 39B and as light as 9C and 11 B. Areas exposed to the sun moderately blush to as dark as between 46D and 47B. At the point where the petal attaches, there is a somewhat small zone of near 9A.

The upper surface color of the intermediate and inner petals is similarly colored to the upper surface color of the outer petals with no blush color.

The general tonality of the newly opened flower is between 9C and 11B washed with between 37C and 38D and sometimes irregularly flecked and striped with as dark as between 37A and 39B and as light as 9C and 11B. The outermost petals are usually blushed to as dark as between 46D and 47B.

THREE-DAY-OLD FLOWER

The under surface color of the outer, intermediate and inner petals is between 11C and 13D. There is no visible change in coloration at the point where the petal attaches.

The upper surface color of the outer, intermediate and inner petals is between 9D and 11C. Areas exposed to the sun heavily blush with as dark as between 53B and 47A, sometimes irregularly flecked and striped with as light as between 13D and 11D to as dark as between 53B and 47A. At the point where the petal attaches, there is a very small zone of near 11B.

The general tonality of the three-day-old flower is between 9D and 11C, usually heavily blushed with as dark as between 53B and 47A and sometimes irregularly flecked and striped with as light as between 13D and 11D to as dark as between 53B and 47A.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about three to four days.

MALE REPRODUCTIVE ORGANS

Stamens are average in number (average about 75) and are arranged regularly about the pistils. The filaments are moderately uneven in length (about 0.3 to about 0.9 cm.) most with anthers. Filaments are near 14A in color. The anthers are of small to medium size for the class and all open approximately at the same time. Anther color when immature is near 14D. Anther color at maturity is near 163B on the external part and near 165A on the internal part. Pollen is moderate to abundant and near 12C in color.

FEMALE REPRODUCTIVE ORGANS

Pistils vary in number (average about 45). The styles are somewhat uneven, average to long in length (about 0.3 to about 0.8 cm.), somewhat thin in caliper, and moderately loosely bunched. Stigma color is near 3D. Style color is near 3D at the base, blushing to 46A toward the stigma. Ovaries are usually all enclosed in the calyx.

Hips are somewhat short to average in length (about 1.6 to about 2.2 cm.), very globular in form, and near 30C in color when ripe. The hip surface is usually smooth with moderately thick fleshy walls. The sepals are usually fugacious.

The seeds are irregularly rounded, smooth in texture, approximately 7 to about 12 per hip, about 0.3 to about 0.5 cm. in diameter at the widest point and near 165C in color.

FOLIAGE

The compound leaves are usually comprised of three to five leaflets and are borne abundantly. The five-leaflet leaves are about 10.3 to about 14.6 cm. in length and about 8.6 to about 11.0 cm. in width at the widest point, moderately heavy in texture, and very glossy to somewhat rugose in finish on the upper side and very matte in finish on the under side. The terminal leaflets are about 4.8 to about 6.5 cm. in length and about 3.2 to about 3.9 cm. in width at the widest point, shaped moderately oval to somewhat ovate with very acute apices and somewhat round to acute bases. Their margins are usually simply serrate.

The upper surface color of the mature leaf is between 147A and 137A. The under surface color of the mature leaf is between 147B and 137C. The upper surface color of the young leaf is between 147A and 137A, moderately suffused, especially toward the leaf edge, with between 187A and 183A. The under surface color of the young leaf is between 147B and 137C, heavily suffused with between 187A and 183A.

The rachis is average to heavy in caliper and very rough. The upper side is shallowly grooved with many stipitate glands on the edges of the grooves. The under side of the rachis is very rough with some stipitate glands and many small to medium size prickles. The rachis color is near 137C on the under side, sometimes lightly blushed with near 183C on the upper side.

The stipules are about 1.1 to about 2.0 cm. in length and moderately narrow to medium in width (about 0.6 to about 0.9 cm.) with medium length straight points that usually turn out at an angle of more than 45 degrees. The stipule color is near 137C.

The petiole is average to heavy in caliper and very rough. The upper side is shallowly grooved with many stipitate glands on the edges of the grooves. The under side of the petiole is very rough with some stipitate glands and many small to medium size prickles. The petiole is about 0.1 to about 0.3 cm. in length and about 0.1 cm in diameter at the widest point. The petiole color is near 137C on the under side, sometimes lightly blushed with near 183C on the upper side.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a spreading climbing growth habit with canes about 300 cm. to about 350 cm. in length with full branching. It displays very vigorous growth and the canes are of medium to heavy caliper for the class (about 1.4 to about 2.5 cm. in width at the widest point).

The color of the major stems is near 148B. They bear numerous prickles of many sizes which range from about 0.3 to about 1.2 cm. in length. The larger prickles are almost straight and angled moderately downward with a medium length moderately narrow base; large prickle coloration is between 160B and 163D. The smaller prickles are almost straight with a short narrow base and of similar coloration.

The color of the branches is between 138A and 146A. They bear numerous prickles of many sizes which are of similar size and shape to the prickles on the major stems; prickle color is near 166C.

The color of the new shoots is between 138A and 143A sometimes lightly suffused with near 183B. They bear numerous prickles of many sizes which are of similar size and shape to the prickles on the major stems; prickle color is between 160B and 163D.

I claim:

1. A new and distinct Climbing rose plant of the variety substantially as described and illustrated herein.

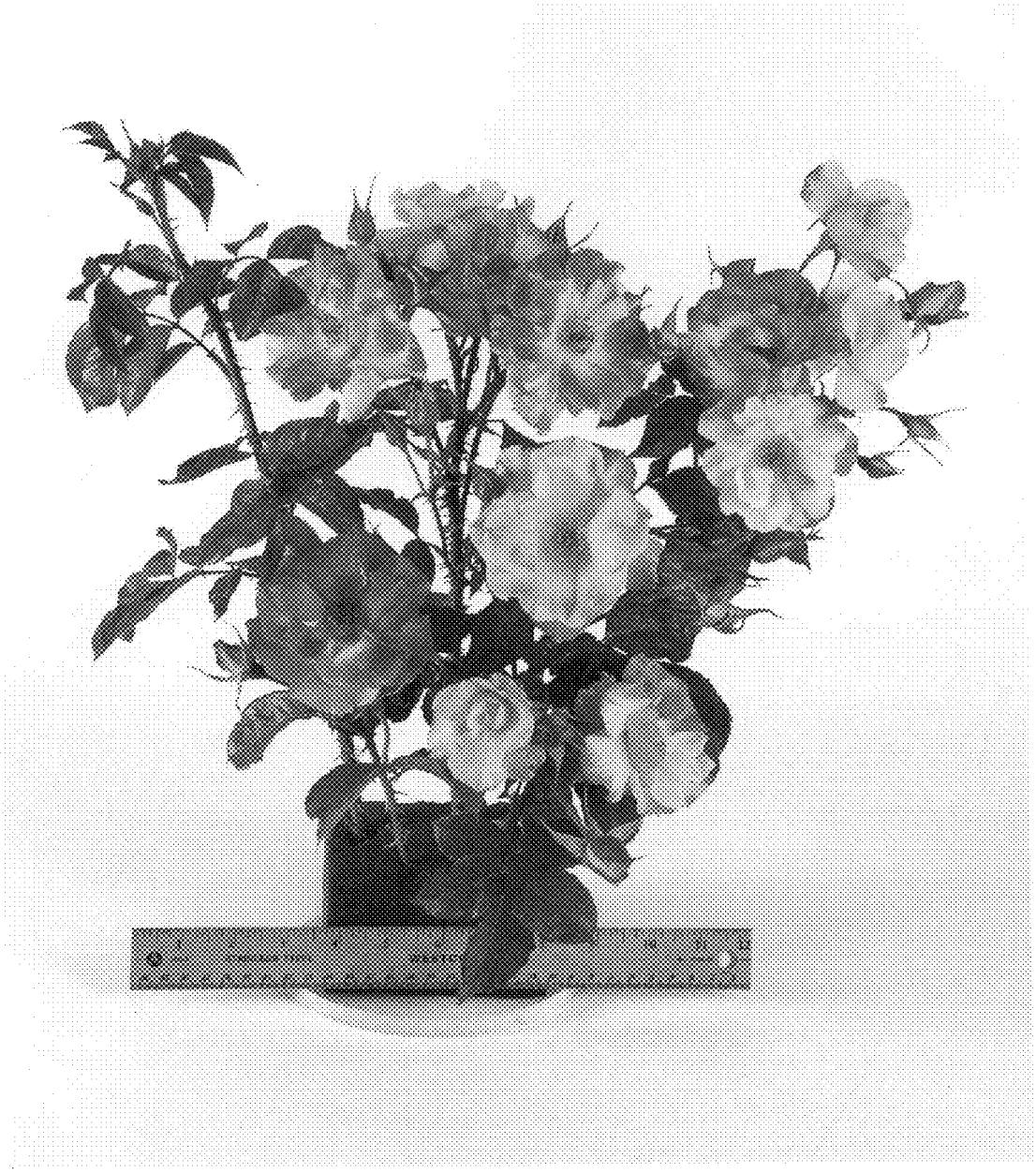

* * * * *